United States Patent
Davis

(10) Patent No.: US 9,457,121 B1
(45) Date of Patent: Oct. 4, 2016

(54) ULTRAVIOLATE LIGHT STERILIZATION APPARATUS

(71) Applicant: Matthew Phillip Davis, Columbia, MO (US)

(72) Inventor: Matthew Phillip Davis, Columbia, MO (US)

(*) Notice: Subject to any disclaimer, the term of this patent is extended or adjusted under 35 U.S.C. 154(b) by 0 days.

(21) Appl. No.: 14/987,419

(22) Filed: Jan. 4, 2016

Related U.S. Application Data

(63) Continuation-in-part of application No. 14/660,400, filed on Mar. 17, 2015, now abandoned.

(51) Int. Cl.
*A61N 5/06* (2006.01)
*A61L 9/20* (2006.01)
*A61M 16/01* (2006.01)
*A61M 16/00* (2006.01)

(52) U.S. Cl.
CPC ............. *A61L 9/20* (2013.01); *A61M 16/0057* (2013.01); *A61M 16/01* (2013.01)

(58) Field of Classification Search
CPC .................................. C02F 1/325; C02F 1/32
USPC .................................. 250/432 R, 436, 504 R
See application file for complete search history.

(56) References Cited

U.S. PATENT DOCUMENTS

| | | | | |
|---|---|---|---|---|
| 5,855,203 A * | 1/1999 | Matter | ...................... | A61L 2/10 128/207.14 |
| 6,470,888 B1 * | 10/2002 | Matter | ...................... | A61L 2/10 128/207.14 |
| 9,295,742 B2 * | 3/2016 | Rasooly et al. | .......... | A61L 2/10 |
| 2012/0321509 A1 * | 12/2012 | Bak | ........................... | A61L 2/10 422/24 |

* cited by examiner

*Primary Examiner* — Michael Maskell
(74) *Attorney, Agent, or Firm* — Dak J. Ream

(57) ABSTRACT

A sterilization apparatus for sterilizing air includes an outer housing having side walls extending between opposed bottom and top walls that, together, define an outer chamber. An inner housing is situated in the outer chamber and includes opposed top and bottom ends and having a wall structure that defines a sealed inner chamber extending therebetween. The wall structure includes at least one side wall that defines a transparent window. An inlet port is in communication with one end of the inner chamber and that directs unsterilized air into the inner chamber. An ultraviolet ("UV") light source is positioned outwardly adjacent the window and configured to emit UV light through the window and into the inner chamber when energized so as to sterilize air in the inner chamber. An outlet port is in communication with another end of the inner chamber that directs sterilized air downstream from the inner chamber.

19 Claims, 14 Drawing Sheets

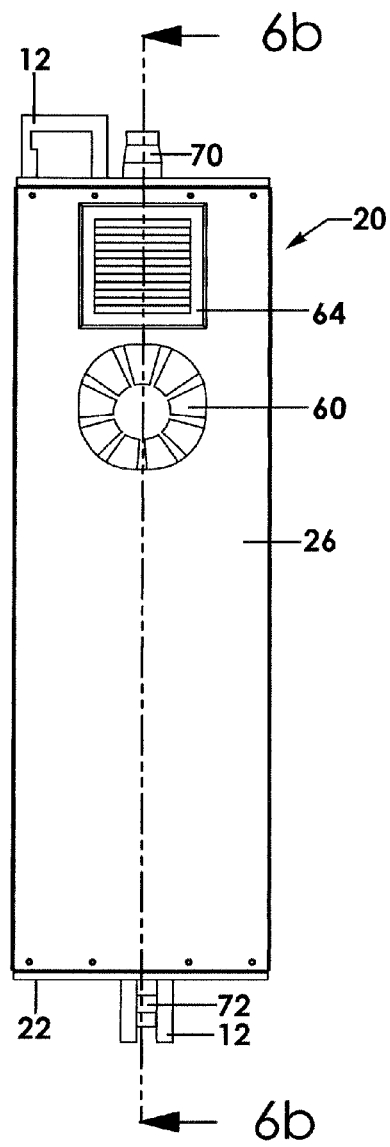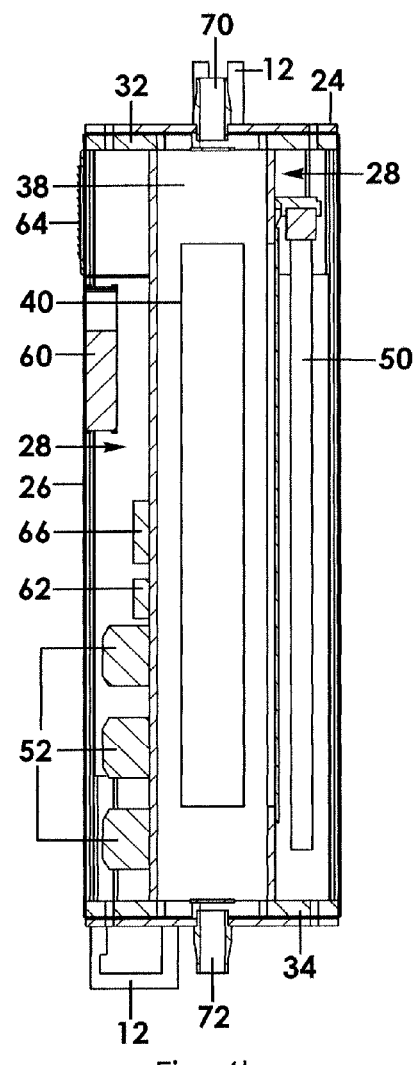
Fig. 6a
Fig. 6b

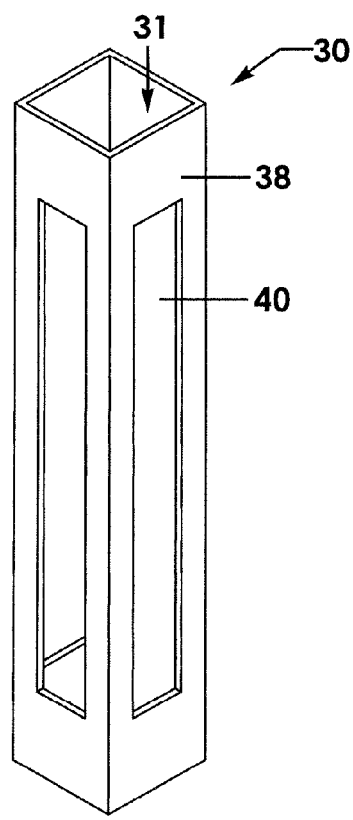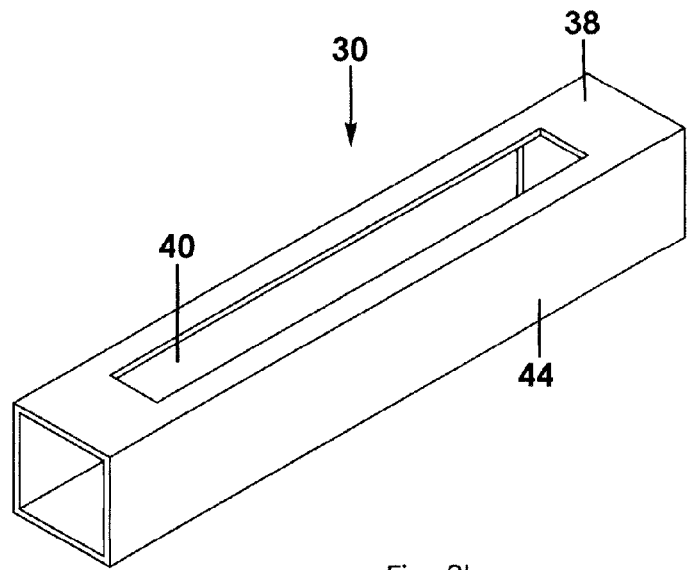
Fig. 8a
Fig. 8b

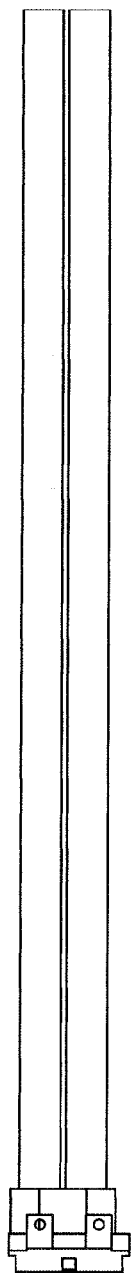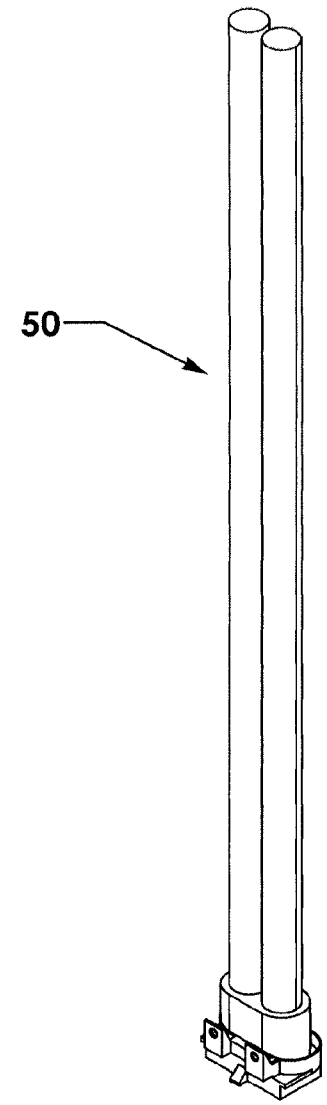
Fig. 9a
Fig. 9b

ULTRAVIOLATE LIGHT STERILIZATION APPARATUS

REFERENCE TO RELATED APPLICATIONS

This application claims the benefit of provisional patent application U.S. Ser. No. 14/660,400 filed Mar. 17, 2015 titled LUMENIZATION and which is incorporated completely herein by reference.

BACKGROUND OF THE INVENTION

This invention relates generally to sterilization devices and, more particularly, to an apparatus using ultraviolet light for sterilizing a patient's breath.

Hospital acquired infections, also known as nosocomial infections, are considered a top five cause of death according to the CDC, with as many as 1.7 million acquired infections every year. Anesthesia machines and ventilators are considered life-support equipment since they provide artificial breathing to individuals. Due to the cycle of air, and repeated processes on a multitude of individuals, each machine will begin to accumulate bacteria in the internal pneumatics. This bacteria, which is trapped is a potential cause for nosocomial infection, since many patients have typically just entered or exited surgery. This in combination with the number of surgeries between preventative maintenance schedules allows months of bacterial and viral build up prior to being sterilized. On average most companies involved in life support require preventative maintenance every 6 months, which allows months of bacterial and viral buildup prior to being addressed and sterilized.

Therefore, it would be desirable to have a sterilization apparatus that can be inserted into the cyclical stream of inhalation and exhalation of a medical patient that can sterilize unsterilized air passing from a patient's own breathing or circulating through a ventilator, respirator, or other anesthesia equipment before again going to a patient. Further, it would be desirable to have a sterilization apparatus that sterilizes a patient air stream by applying ultraviolet light to the air as it passes through the sterilization apparatus.

SUMMARY OF THE INVENTION

The sterilization apparatus according to the present invention sterilizes a patient's exhaled breath, which in return sterilizes the internal pneumatics of anesthesia machines and ventilators. Of course, the sterilization apparatus may be configured to sterilize air before it reaches a patient—thus providing sterilized air to the patient. In use, an entire cycle of air involves sterilizes exhaled air for use as inhaled air back to the patient. Use of the present apparatus prevents or reduces future infections from occurring since the machines would stay sterilized internally.

Specifically, an ultraviolet light sterilization apparatus for use in sterilizing air in connection with an anesthesia or ventilator device includes an outer housing having opposed bottom and top walls and a plurality of outer housing side walls extending between the opposed bottom and top walls that, together, define an outer chamber. An inner housing is situated in the outer chamber and having opposed top and bottom ends and having a wall structure that defines a sealed inner chamber extending between the top and bottom ends, the wall structure defining an inner chamber. The wall structure includes at least one side wall that defines a transparent window.

An inlet port is in fluid communication with one end of the inner chamber and configured to direct unsterilized air into the inner chamber. An ultraviolet ("UV") light source is positioned outwardly adjacent the window and configured to emit UV light through the window and into the inner chamber when energized so as to sterilize air in the inner chamber. An outlet port is in fluid communication with another end of the inner chamber and configured to direct sterilized air downstream from the inner chamber, such to a respirator and back to the patient.

The invention relies on UV-C sterilization to target the bacteria, viruses, and spores found in the internal pneumatics of these pieces of equipment. Since UV-C is between 250-280 nm it is able to deactivate bacteria by destroying its genetic material. It is able to penetrate into the cells of these microorganisms and break their DNA strands, essentially disabling their ability to reproduce. Since they are unable to reproduce they are considered inactive, and are no longer considered harmful. UV sterilization is used in operating rooms currently for the sterilization of external microorganisms, but is ineffective against internal bacteria, viruses, and protozoa. It is also contemplated that UV-C light emitting diodes (LEDs) may also be utilized in some embodiments.

The process of sterilization was to take the maximum flow rate of 15 L/min from a standard internal 15 mm diameter patient circuit and increase the diameter in order to slow velocity to achieve a 2-10 second time gap based off of linear velocity of the cycle. This allows the UV-C light to sterilize with 99.99% effectiveness of sterilization. The device would be introduced into the exhalation side of the patient circuit and is retrofitted with bacteria filters on both sides of the device to remove larger organisms from entering the machine.

UV dosage was addressed according to a study done by Crystal IS, who specializes in UV-C sterilization for HVAC systems. Their study concluded a log reduction of 6 levels, which increased the effectiveness of UV-C sterilization. They tested 29 bacterias, 29 protozoas, and 58 viruses for peak UV dosages. They found that a max dosage of 235 mJ/cm2 would effectively sterilize all bacteria, protozoa, and viruses at 99.9999% effectiveness when exposed for 2-10 seconds.

Since the present apparatus targets the exhalation cycle of the patient, it does not affect delivered flow rates or percentages of oxygen, nitrous oxide, medical air, sevoflurane, desflurane, isoflurane, or any other type of gas, which may be delivered to the patient.

In an embodiment, the device may be equipped with a power supply and heat sync in order to provide power to the UV-C LED bulbs, and dissipate heat. The output of each LED bulb is 100 mW/cm2, so a minimum of three LED bulbs is needed in order to effectively achieve the UV dosage. The internal shroud of the device is reflective in order to decrease dosage absorption into the material, and increase effectiveness.

In addition to the present sterilization apparatus, ventilators and anesthesia machines both use bacteria filters, and soda lime to scrub CO2 and remove moisture from the air. This device helps trap moisture, while also removing infectious material.

Therefore, a general object of this invention is to provide a sterilization apparatus that destroys and sterilizes air exhaled by a patient before the air is returned to the patient.

Another object of this invention is to provide a sterilization apparatus, as aforesaid, that applies ultraviolet light to an air stream exhaled by a patient so as to sterilize the air of virus and other contaminants.

Still another object of this invention is to provide a sterilization apparatus, as aforesaid, that cleanses the air flowing from a respirator, ventilator, or anesthesia device that may have picked up bacterial or viral buildup.

Yet another object of this invention is to provide a sterilization apparatus that may be inserted into the normal flow of anesthesia and respiration equipment used during surgical procedures.

A further object of this invention is to provide a sterilization apparatus, as aforesaid, that functions without manual interaction.

Other objects and advantages of the present invention will become apparent from the following description taken in connection with the accompanying drawings, wherein is set forth by way of illustration and example, embodiments of this invention.

BRIEF DESCRIPTION OF THE DRAWINGS

FIG. 1a is a front view of a ultraviolet light sterilization apparatus according to a preferred embodiment of the present invention;

FIG. 1b is a perspective view of the sterilization apparatus as in FIG. 1a;

FIG. 5a is a side view of the sterilization apparatus as in FIG. 4 illustrated with the light assemblies removed;

FIG. 5b is a perspective view of the sterilization apparatus as in FIG. 5a;

FIG. 6a is a front view of the sterilization apparatus as in FIG. 1a;

FIG. 6b is a sectional view taken along line 6b-6b of FIG. 6a;

FIG. 7a is a side view of the sterilization apparatus as in FIG. 1b;

FIG. 7b is a sectional view taken along line 7b-7b of FIG. 7a;

FIG. 8a is a perspective view of an inner housing removed from the outer housing of the sterilization apparatus;

FIG. 8b is a perspective view of the inner housing as in FIG. 8a taken from another angle;

FIG. 9a is a front view of a light assembly removed from the outer housing of the sterilization apparatus;

FIG. 9b is a perspective view of the light assembly as in FIG. 9a;

DESCRIPTION OF THE PREFERRED EMBODIMENT

Figure 1:
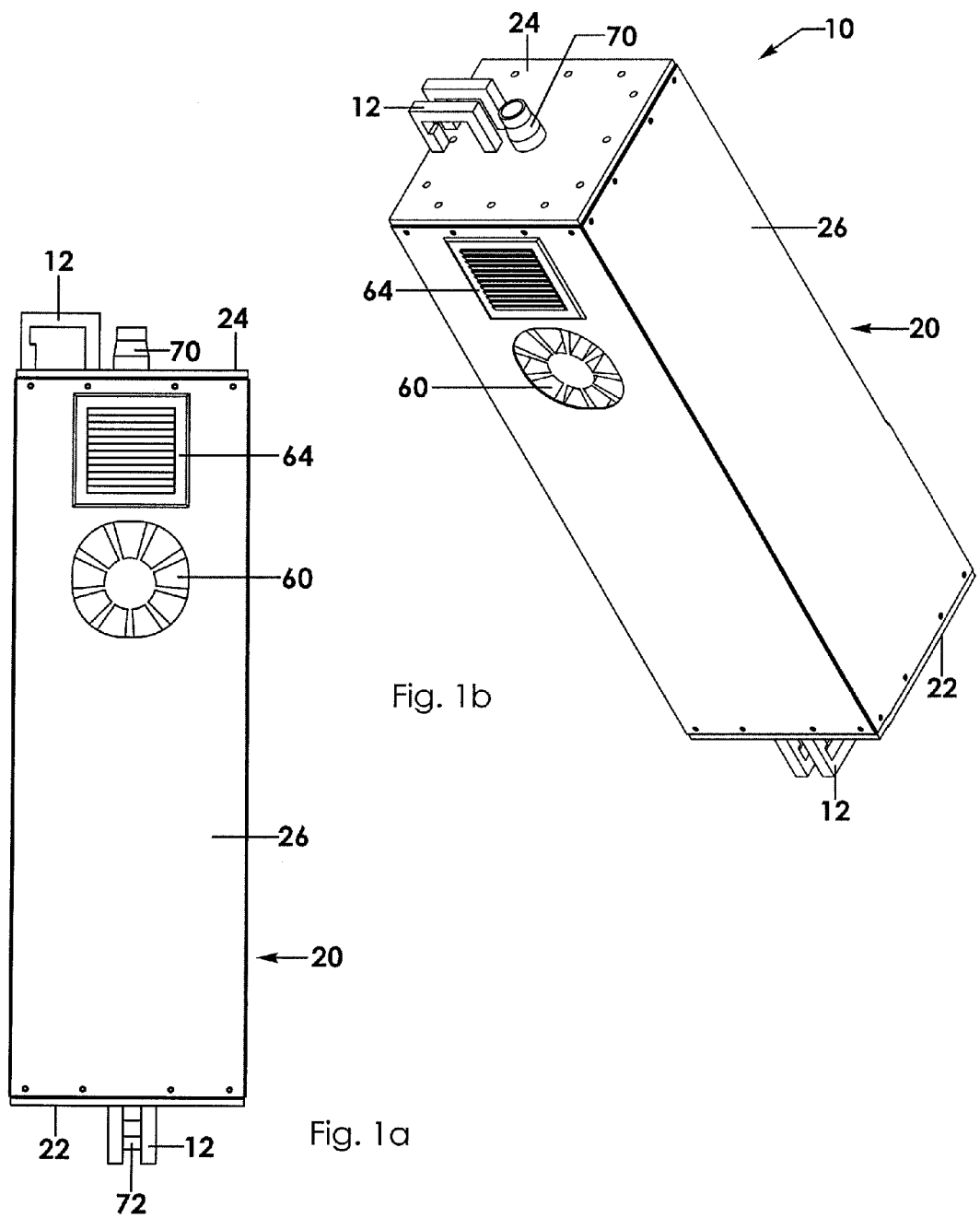

A sterilization apparatus according to a preferred embodiment of the present invention will now be described in detail with reference to FIGS. 1a to 14 of the accompanying drawings. The sterilization apparatus includes an outer housing 20, an inner housing 30, a plurality of ultraviolet ("UV") light assemblies 50, and connections to upstream and downstream exhalation airflows to and from a medical patient.

The outer housing 20 includes a bottom wall 22 and an opposed top wall 24, each having a generally planar configuration. In an embodiment, a plurality of outer housing side walls 26 extends between corresponding peripheral edges of respective bottom and top walls. Together, the side, top, and bottom walls define an interior space, hereafter referred to as an outer chamber 28. The outer housing 20 may be sealed airtight except as otherwise noted below as ambient air will be routed through the outer housing 20. The top wall 24 and the bottom wall 22 of the outer housing 20 define an aperture through which an inlet port 70 and an outlet port 72 extend, respectively, as will be described later.

Figure 2:
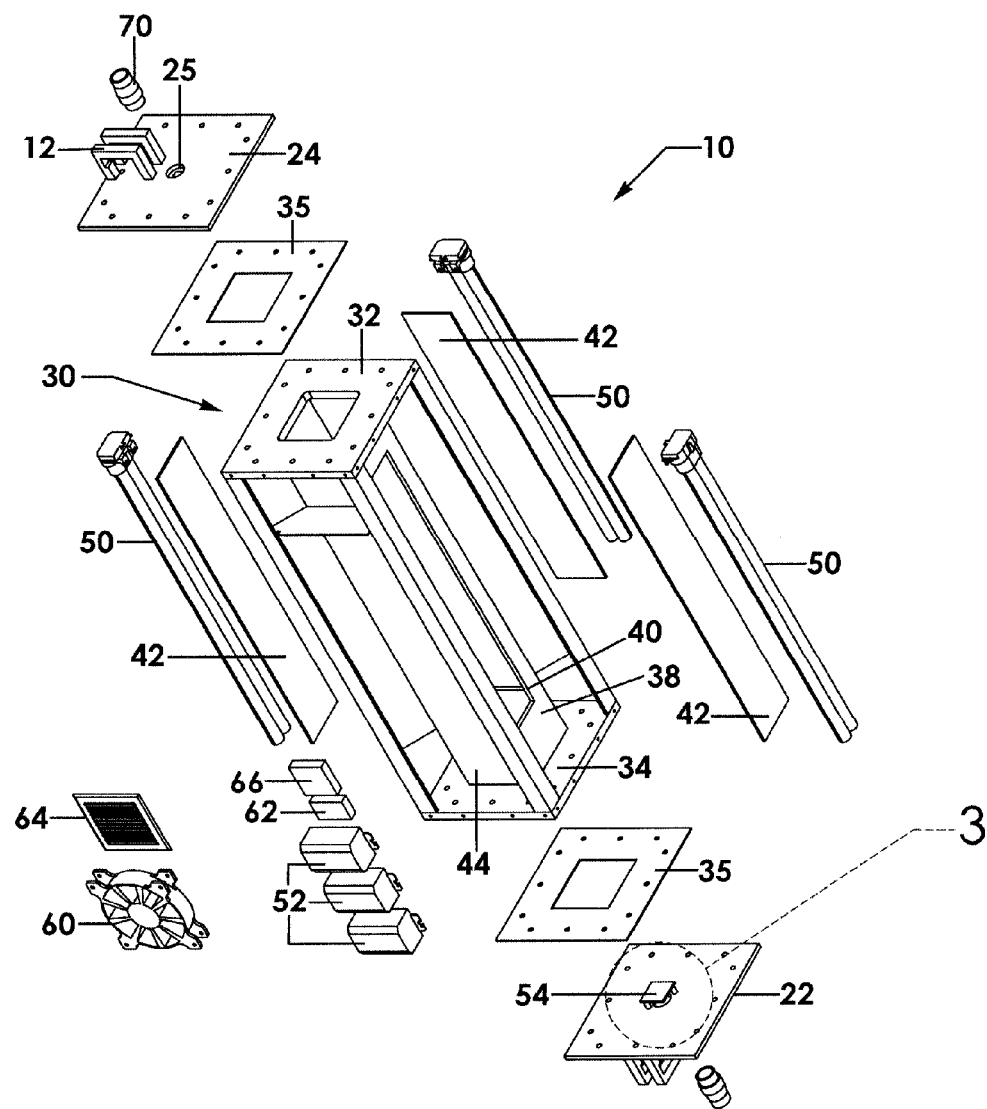
FIG. 2 is an exploded view of the sterilization view as in FIG. 1b.
Figure 3:
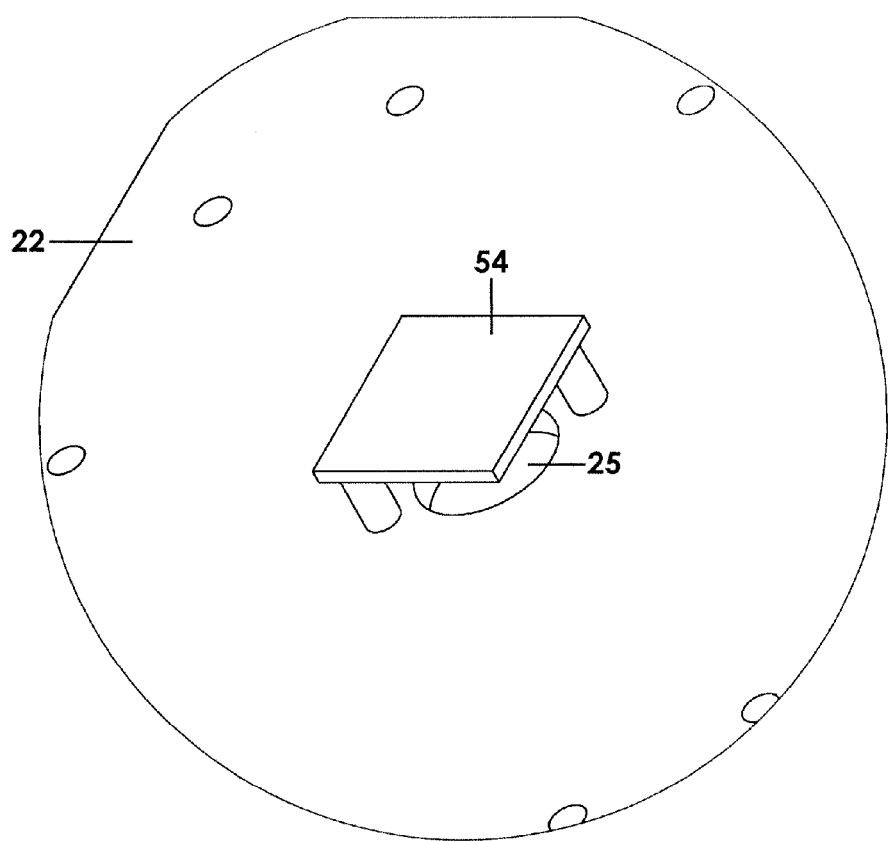
FIG. 3 is an isolated view on an enlarged scale taken from FIG. 2.

The inner housing 30 may include a top end 32 and a bottom end 34 and have a wall structure 36 extending therebetween. It is noted that the top and bottom ends of the inner housing 30 may also be planar structures and the wall structure 36 is inwardly displaced from respective peripheral edges of the top and bottom ends (FIG. 2). The bottom wall 22 of the outer housing 20 may be coupled to the bottom end 34 of the inner housing. Likewise, the top wall 24 of the outer housing 20 may be coupled to the top end 32 of the inner housing 30. In an embodiment, a gasket 35 may be sandwiched between respective bottom wall/bottom end and top wall/top end to enhance an airtight seal (FIG. 2). The inner housing 30 is positioned within the interior area, i.e. the outer chamber 28. The combinations of the bottom wall/bottom end and top wall/top end structures seal the inner chamber 31 from ambient air. Each of these structures also defines an aperture, opening, or channel through which the outlet port 72 and inlet port 70 extend and are in fluid communication with the inner chamber 31, respectively.

Now more particularly, the wall structure 36 of the inner housing 30 may include three side walls 38 configured perpendicular to one another and that each define a window 40 extending substantially between the top end 32 and bottom end 34. Each window 40 is covered or filled with a transparent panel 42, such as a plastic or acrylic sheet such as that marketed under the trade name Plexiglas™. The wall structure 36 may include a fourth side wall 44 that is solid and opaque and that does not include a window. Together, the side walls, top end, and bottom end define an airtight/sealed interior space referred to hereafter as an inner chamber 31. The side walls of the inner housing 30 may be arranged in an elongate rectangular configuration although other configurations would also work.

Figure 4:
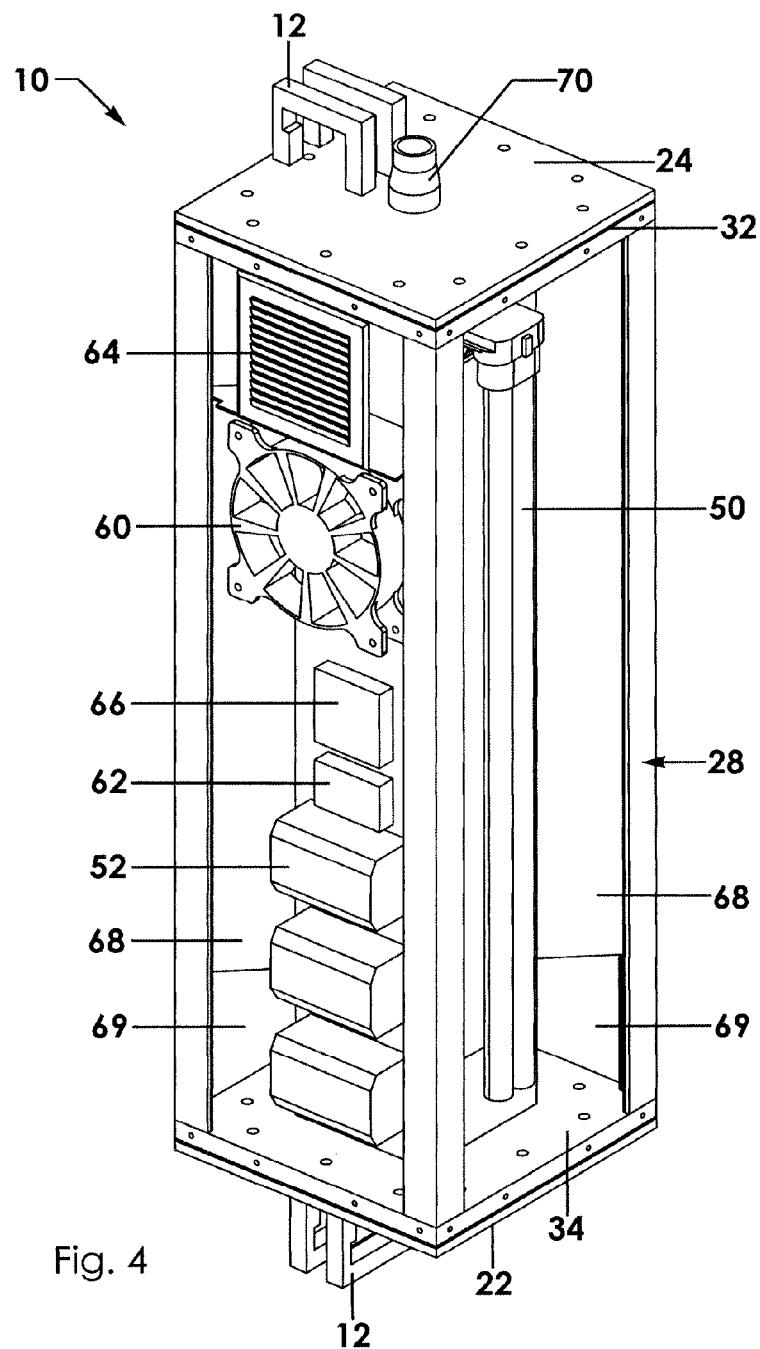
FIG. 4 is a perspective view of the sterilization apparatus as in FIG. 1b illustrated with the side walls of the outer housing removed for clarity.
Figures 5A, 5B:
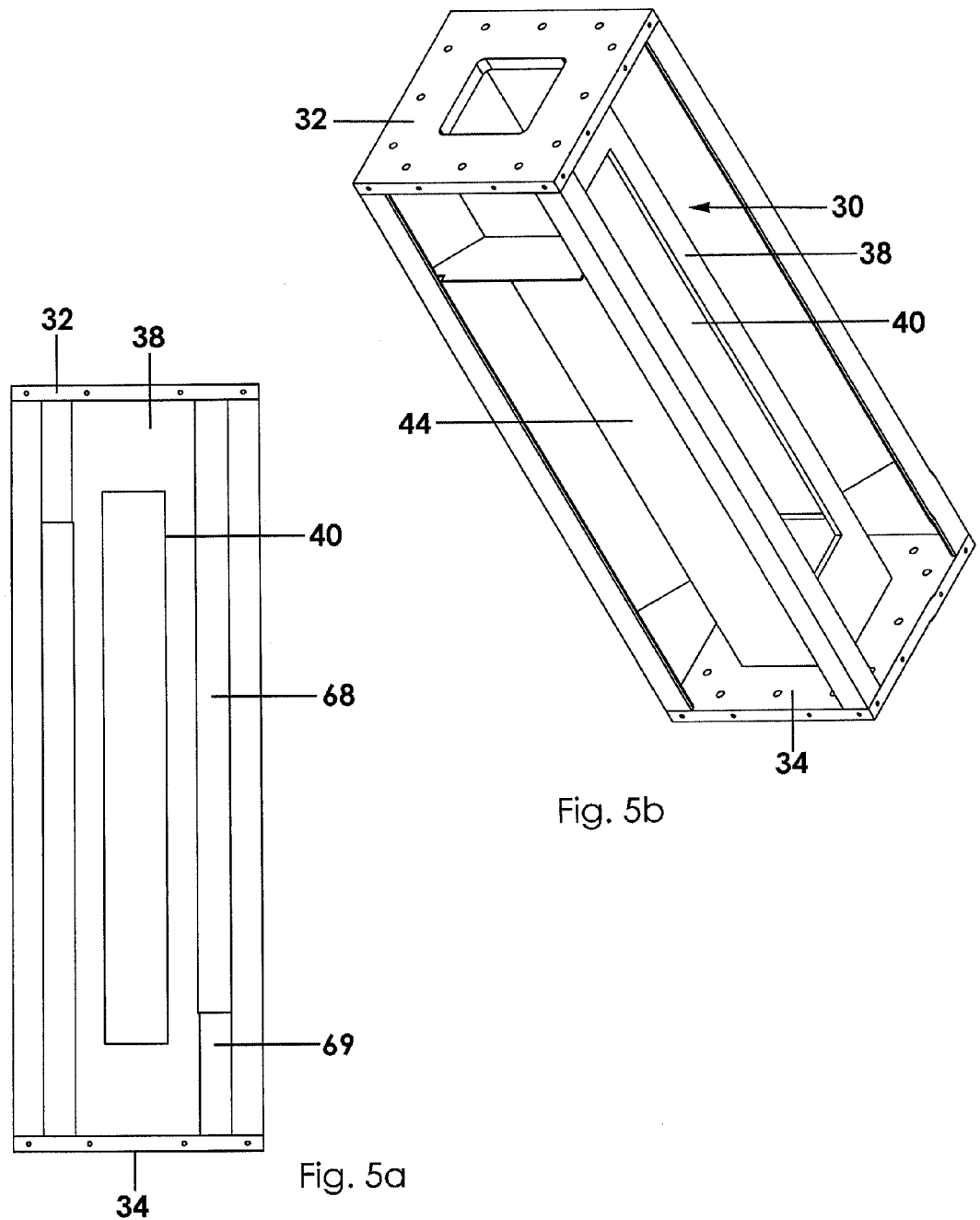
Figures 7A, 7B:
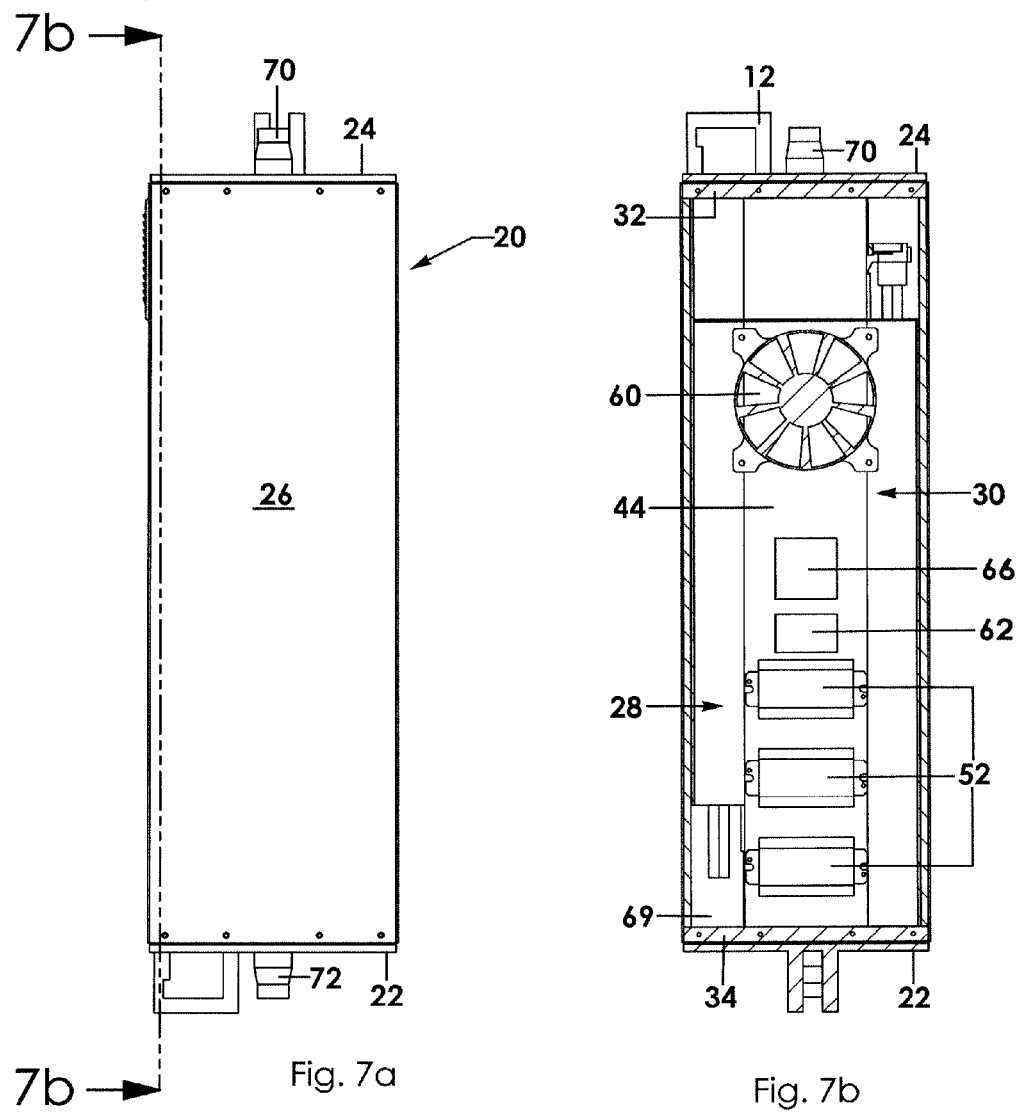

At least one UV light source is positioned adjacent at least one transparent window 40; preferably, however, a plurality of ultraviolet light assemblies 50 ("UV lights") may be positioned outwardly adjacent respective windows 40 of the side walls 38 of the inner housing 30 (FIGS. 4 and 6b). More particularly, three spaced apart UV light assemblies may be situated in the outer chamber adjacent respective windows. In one embodiment, each UV light assembly 50 may include a single or dual UV light bulb positioned within the outer chamber so as to direct UV light into the inner chamber 31 through respective windows 40. It is also contemplated that UV-C light emitting diodes (LEDs) may also be utilized in some embodiments.

A ballast 52 is electrically connected to each UV light assembly 50 and, as such, controls the operation thereof. Specifically, the ballast 52 actuates the UV light assembly 50 to emit UV light directly into the inner chamber 31 via respective windows 40 when energized. The ballasts, collectively, may be mounted to the fourth side wall 44 that does not define a window 40 (FIG. 4). A ballast, used in a lighting system, regulates the current to the lamps and provides sufficient voltage to start the lamps. An ultraviolet light, in the same manner as a fluorescent lamp, connected directly to a high voltage power source would rapidly and uncontrollably increase its current draw if not for the function of a ballast to limit its current. Within a second the light assembly would overheat and burn out. During startup of a light, the ballast must briefly supply high voltage to establish an arc between two electrodes. Once the arc is established, the ballast quickly reduces the voltage and regulates the electric current to produce a steady light output. In the present invention, a electric power converter 62 may also be mounted to the fourth side wall 44 (or otherwise situated in the outer chamber 28) and be in electrical communication with each ballast 52 so that the UV light assemblies may be energized and controlled.

A reflective light shield 54 is coupled to an inner surface of the bottom wall 22 of the outer housing 20 and is situated to cover the aperture 25. However, the light shield 54 is slightly displaced from the aperture 25 so as not to block airflow but, rather, to reflect UV light back into the inner chamber 31 and not into the outlet port 72. Similarly, another reflective light shield 54 is coupled to an inner surface of the top wall 24 of the outer housing 20.

In another aspect, the sterilization apparatus 10 may include a cooling system configured to dissipate heat that may build up from operation of the multiple UV light assemblies. In an embodiment, a cooling fan 60 is situated in the outer chamber 28 and may be coupled to a selected outer housing side wall 26 and configured to draw ambient air into the outer chamber 28. The cooling fan 60 may be electrically connected to a power converter 62 or other power source. In addition, an exhaust vent 64 is situated in an outer side wall 26 and configured to direct air out or away from the outer chamber 28, the exhausted air being pushed by incoming air as will be described below. A baffle or system of baffles may separate ambient air drawn into the outer chamber 28 from the cooling fan 60 from air being exhausted by the exhaust vent.

The cooling system may include a temperature sensor 66, which may also be referred to as a temperature switch. The temperature sensor 66 may be also be electrically connected—directly or indirectly—to the cooling fan 60 and configured to actuate the cooling fan 60 to operate when a predetermined temperature is detected within the outer chamber 28. In other words, the cooling fan 60 is energized to pull cooler ambient air into the outer chamber 28 in order to push warmer ambient air out of the outer chamber 28.

The outer housing 20 and outer chamber 28 are configured to channel incoming air so as to maximize its ability to absorb the heat of the light assemblies 50 and to thereby dissipate heat. More particularly, the outer housing 20 may include a plurality of spaced apart baffles 68 or wall panels positioned to divide the outer chamber into a plurality of sub-chambers that control and direct the path of ambient air flowing between the cooling fan 60 and the exhaust vent 64. The baffles 68 may define openings 69 that allow air to flow from one sub-chamber into an adjacent sub-chamber. Specifically, one respective baffle opening 69 may be situated adjacent the bottom wall 22 and a next adjacent baffle opening 69 may be situated adjacent the top wall 24, and so on. In this manner, ambient airflow may pass across each UV light assembly on its path between the cooling fan 60 and the exhaust vent 64. In another embodiment (not shown), a heat sync may be included for dissipating heat.

In addition, a pair of handles 12 is coupled to an outer surface of each of the bottom wall 22 and top wall 24 of the outer housing 20. Preferably, the handles 12 have a U-shaped configuration although a single handle and other shape configurations may also work. The handles 12 make it feasible for a person to pick up and carry the entire sterilization apparatus 10 if desired and may also serve as a means of attachment to a overall breathing system 100 (FIG. 12)

Figure 10:
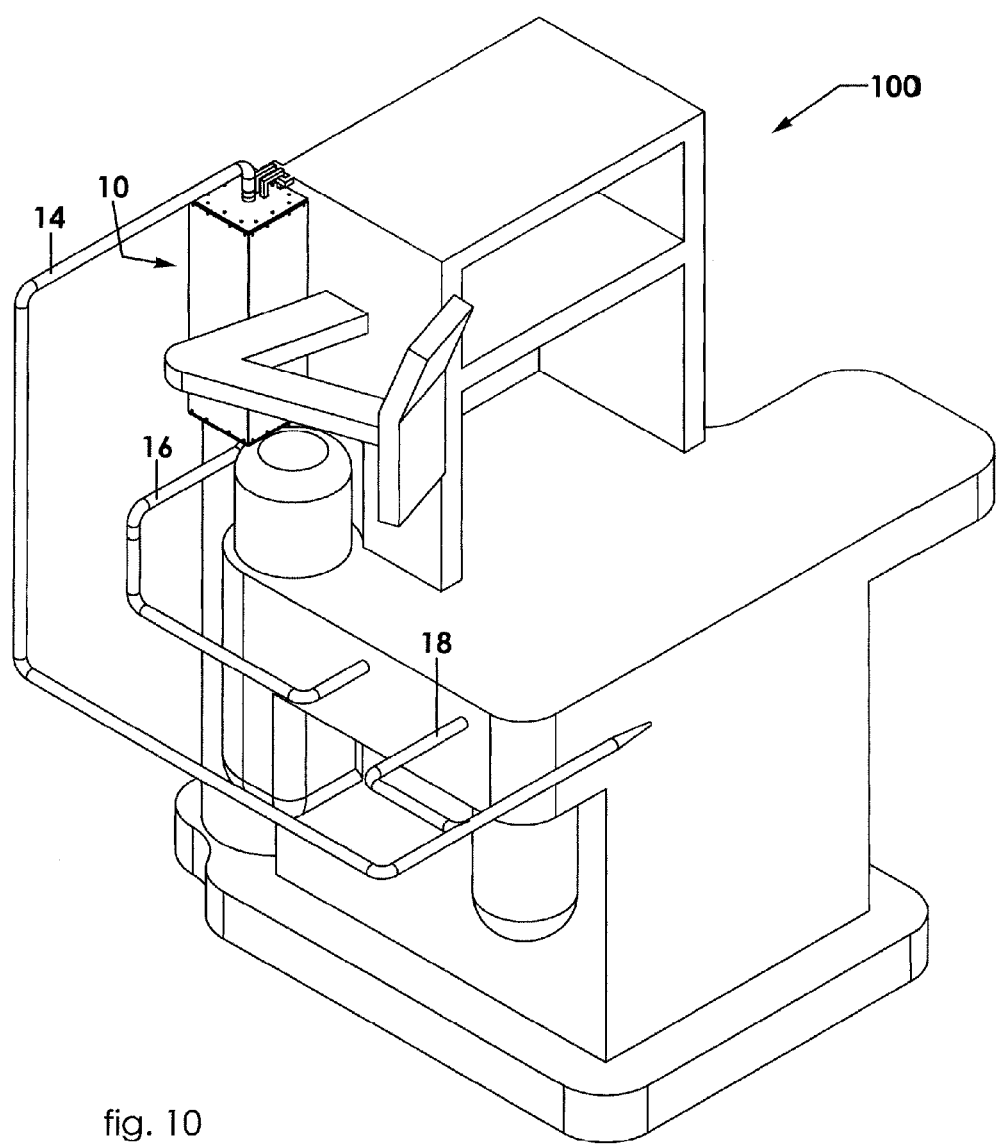
FIG. 10 is a perspective view of the sterilization apparatus mounted to a breathing or anesthesia system.
Figure 11:
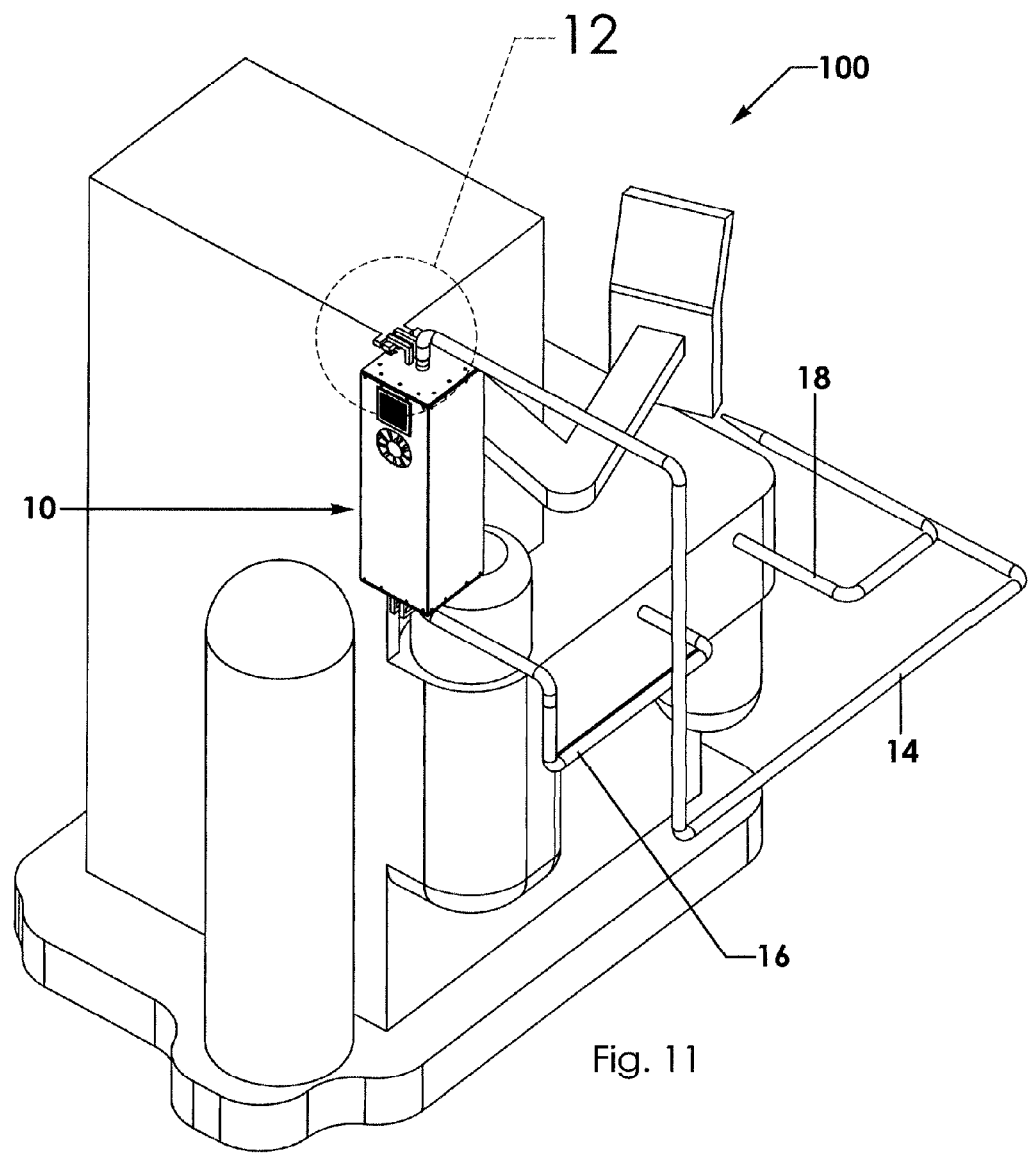
FIG. 11 is another perspective view taken from another angle of the sterilization apparatus as in FIG. 10.
Figure 12:
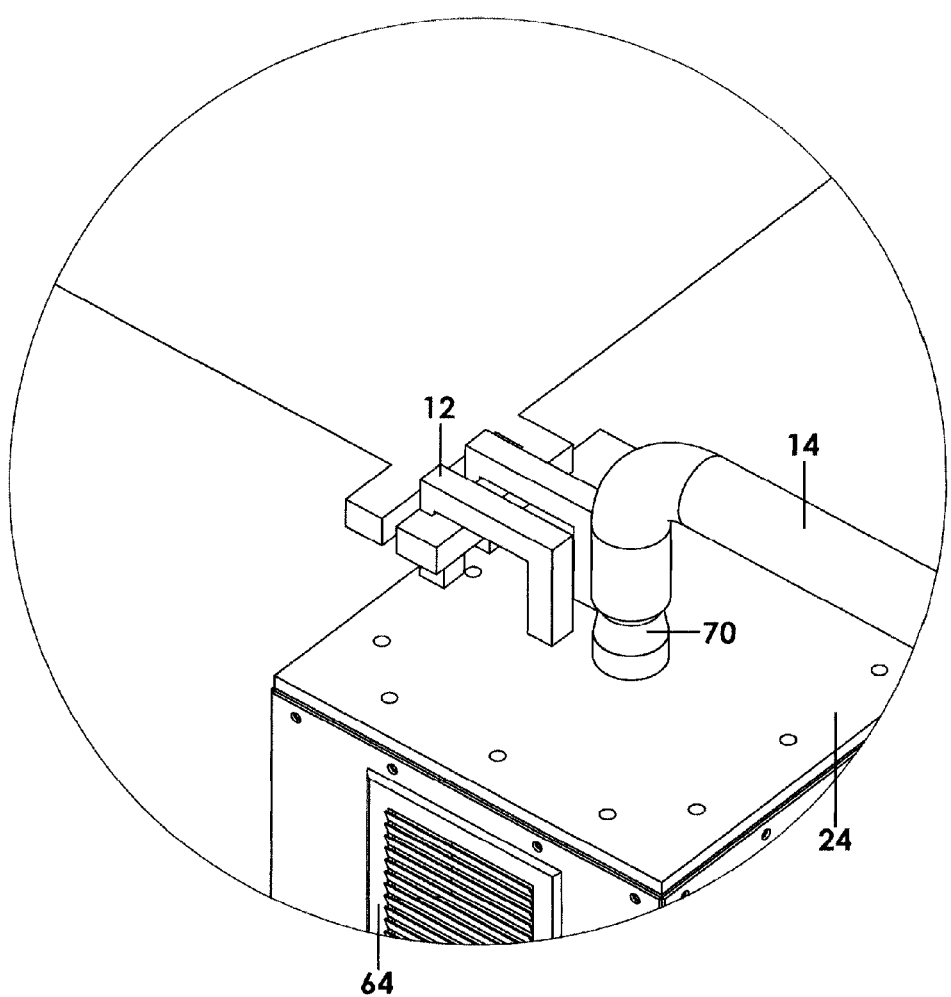
FIG. 12 is an isolated view on an enlarged scale taken from FIG. 11.
Figure 13:
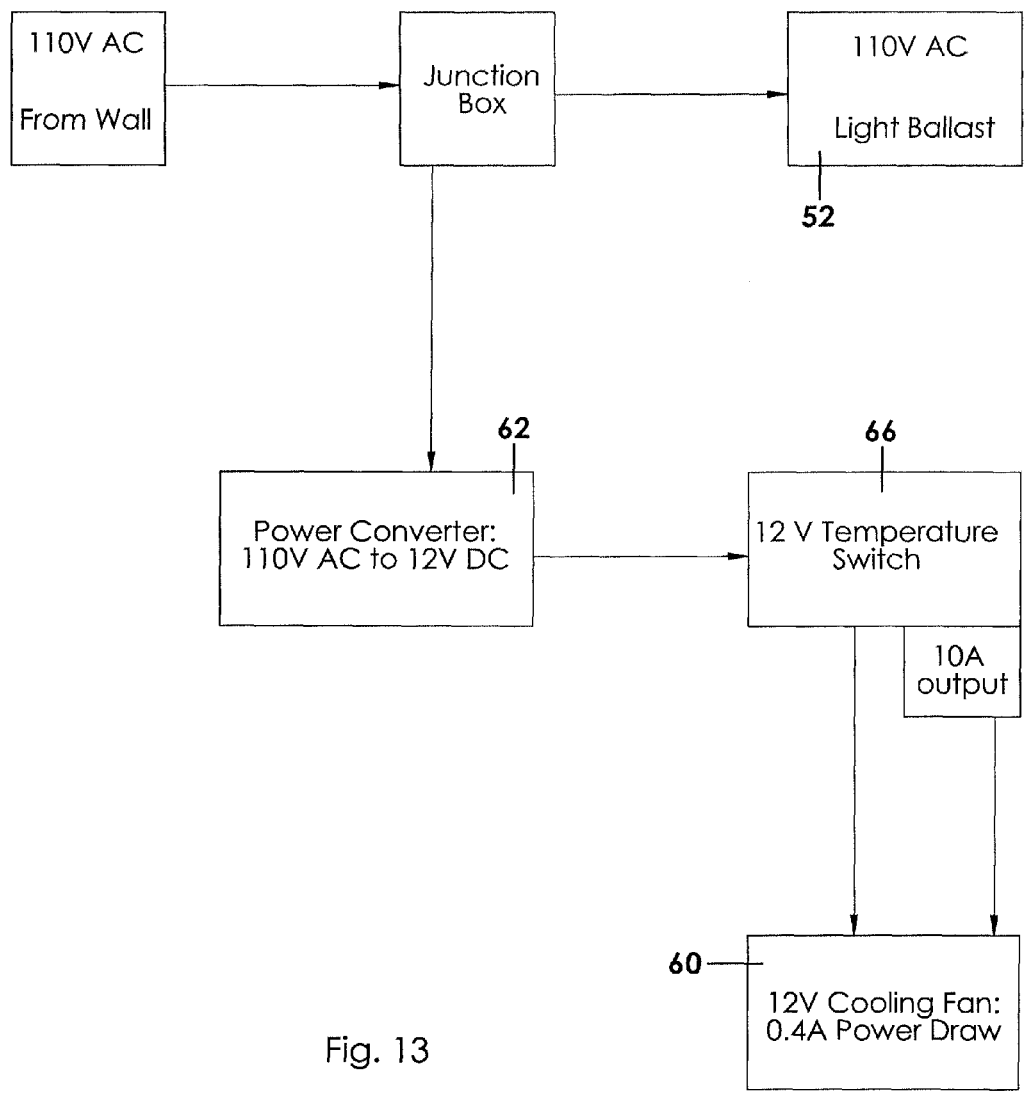
FIG. 13 is a block diagram illustrating the electric, electronic, and motorized components of the present invention.
Figure 14:
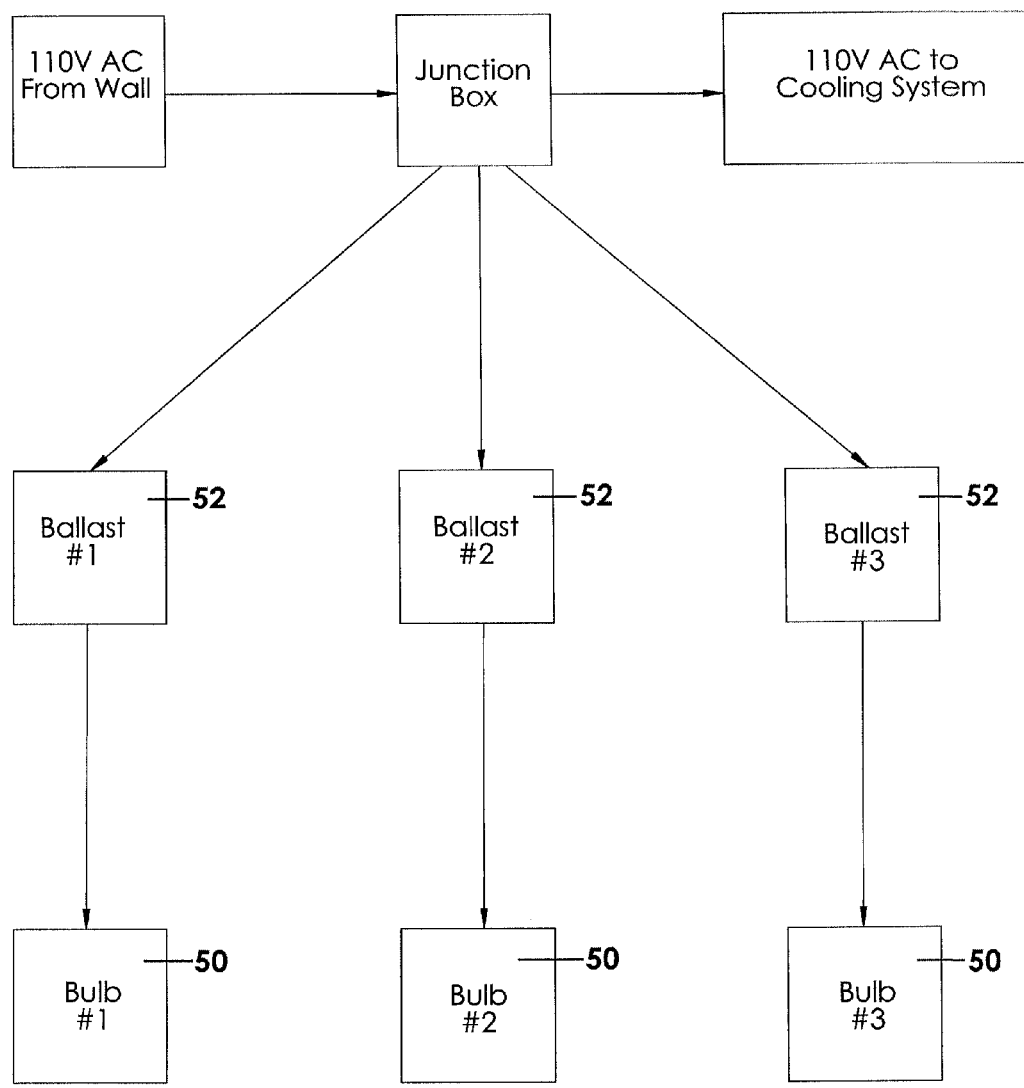
FIG. 14 is a block diagram illustrating the UV lighting components of the present invention.

In use, the ultraviolet light sterilization apparatus 10 may be mounted and connected to an anesthesia or breathing system 100 as shown in FIGS. 10-12. A first air tube 14 may receive the exhalation of a patient's breath, such as during a surgical procedure, the first air tube 14 being operatively connected to the inlet port 70 of the sterilization apparatus 10. Specifically, the unsterilized breath of a patient may be passed into the inner chamber 31 through the inlet port 70 and be sterilized by UV light being directed into the inner chamber 31 as described above. The outlet port 72, on the other hand, may be operatively connected to a second air tube 16 that delivers sterilized air to a respirator or other breathing device. From there, a third air tube 18 returns the sterilized air to the patient.

It is understood that while certain forms of this invention have been illustrated and described, it is not limited thereto except insofar as such limitations are included in the following claims and allowable functional equivalents thereof.

The invention claimed is:

1. A sterilization apparatus for sterilizing air in connection with an anesthesia or ventilator device, comprising:
   an inner housing having opposed top and bottom ends and having a wall structure that defines a sealed inner chamber extending between said top and bottom ends, said wall structure defining an inner chamber;
   wherein said wall structure includes a side wall that defines a window covered by a transparent panel;
   an inlet port in fluid communication with one end of said inner chamber and configured to direct unsterilized air into said inner chamber;
   an ultraviolet ("UV") light source positioned outwardly adjacent said window and configured to emit UV light through said transparent panel and into said inner chamber when energized so as to sterilize air in said inner chamber; and
   an outlet port in fluid communication with another end of said inner chamber and configured to direct sterilized air downstream from said inner chamber;
   wherein:
      said wall structure includes three side walls that each define a window being covered and sealed by a transparent panel, respectively, and includes a fourth side wall having an opaque construction;
      said UV light source includes three spaced apart UV light assemblies, each UV light assemblies being outwardly positioned adjacent said respective transparent panels and configured to emit UV light into said inner chamber via said respective transparent panels.

2. The sterilization apparatus as in claim 1, further comprising:
   an outer housing having opposed bottom and top walls and a plurality of outer housing side walls extending between said opposed bottom and top walls that, together, define an outer chamber;

wherein said inner chamber is positioned within said outer chamber;
wherein said bottom wall of said outer housing seals said inner chamber from ambient air, said bottom wall defining an aperture through which said inlet port extends into communication with said inner chamber.

3. The sterilization apparatus as in claim 2, wherein:
a reflective light shield is coupled to an interior surface of said top wall of said exterior housing so as to cover said aperture therein;
another reflective light shield is coupled to an interior surface of said bottom wall of said exterior housing so as to cover said aperture therein;
said reflective light shield and said another reflective light shield are configured to reflect UV light into said inner chamber and to prevent UV light from passing into said inlet port and said outlet port that extend into said apertures, respectively.

4. The sterilization apparatus as in claim 1, further comprising a ballast electrically connected to each light assembly, respectively, said respective ballasts mounted to said fourth side wall.

5. The sterilization apparatus as in claim 2, further comprising:
a cooling fan coupled to said outer housing and configured to draw ambient air into said outer chamber when energized;
wherein a respective wall of said outer housing defines an exhaust vent configured to direct ambient air out of and away from said outer chamber.

6. The sterilization apparatus as in claim 5, further comprising a temperature sensor situated in said outer chamber that is operatively connected to said cooling fan and configured to actuate said cooling fan if a predetermined temperature is detected.

7. The sterilization apparatus as in claim 2, wherein said outer housing includes a plurality of spaced apart baffles configured to separate said outer housing into a plurality of sub-chambers, each baffle defining a baffle opening that allows airflow from one respective sub-chamber into an adjacent sub-chamber.

8. The sterilization apparatus as in claim 7, wherein a respective baffle opening of one sub-chamber is adjacent said bottom wall and a respective baffle opening of an adjacent sub-chamber is adjacent said top wall, and so on.

9. The sterilization apparatus as in claim 2, further comprising a pair of handles coupled to an outer surface of said top wall of said outer housing and another pair of handles coupled to an outer surface of said bottom wall of said outer housing.

10. A sterilization apparatus for sterilizing air in connection with an anesthesia or ventilator device, comprising:
an outer housing having opposed bottom and top walls and a plurality of outer housing side walls extending between said opposed bottom and top walls that, together, define an outer chamber;
an inner housing situated in said outer chamber and having opposed top and bottom ends and having a wall structure that defines a sealed inner chamber extending between said top and bottom ends, said wall structure defining an inner chamber;
wherein said wall structure includes at least one side wall that defines a transparent window, wherein the outer housing seals the inner housing against ambient air;
an inlet port in fluid communication with one end of said inner chamber and configured to direct unsterilized air into said inner chamber;
an ultraviolet ("UV") light source positioned outwardly adjacent said window and configured to emit UV light through said window and into said inner chamber when energized so as to sterilize air in said inner chamber;
an outlet port in fluid communication with another end of said inner chamber and configured to direct sterilized air downstream from said inner chamber.

11. The sterilization apparatus as in claim 10, wherein:
said top wall of said outer housing seals said inner chamber from ambient air, said top wall defining an aperture through which said inlet port extends into communication with said inner chamber;
said bottom wall of said outer housing seals said inner chamber from ambient air, said top wall defining an aperture through which said outlet port extends into communication with said inner chamber.

12. The sterilization apparatus as in claim 10, further comprising:
a reflective light shield coupled to an interior surface of said top wall of said exterior housing so as to cover said aperture therein;
another reflective light shield coupled to an interior surface of said bottom wall of said exterior housing so as to cover said aperture therein;
wherein said reflective light shield and said another reflective light shield are configured to reflect UV light into said inner chamber and to prevent UV light from passing into said inlet port and said outlet port that extend into said apertures, respectively.

13. The sterilization apparatus as in claim 10, wherein:
said wall structure includes three side walls that each define a window being covered and sealed by a transparent panel, respectively, and providing a fourth side wall having an opaque construction;
said UV light source includes three spaced apart UV light assemblies, each UV light assemblies being outwardly positioned adjacent said respective transparent panels and configured to emit UV light into said inner chamber via said respective transparent panels.

14. The sterilization apparatus as in claim 13, further comprising a ballast electrically connected to each light assembly, respectively, said respective ballasts mounted to said fourth side wall.

15. The sterilization apparatus as in claim 10, further comprising:
a cooling fan coupled to said outer housing and configured to draw ambient air into said outer chamber when energized;
wherein a respective wall of said outer housing defines an exhaust vent configured to direct ambient air out of and away from said outer chamber.

16. The sterilization apparatus as in claim 15, further comprising a temperature sensor situated in said outer chamber that is operatively connected to said cooling fan and configured to actuate said cooling fan if a predetermined temperature is detected.

17. The sterilization apparatus as in claim 10, wherein said outer housing includes a plurality of spaced apart baffles configured to separate said outer housing into a plurality of sub-chambers, each baffle defining a baffle opening that allows airflow from one respective sub-chamber into an adjacent sub-chamber.

18. The sterilization apparatus as in claim 17, wherein a respective baffle opening of one sub-chamber is adjacent said bottom wall and a respective baffle opening of an adjacent sub-chamber is adjacent said top wall, and so on.

19. The sterilization apparatus as in claim 10, further comprising a pair of handles coupled to an outer surface of said top wall of said outer housing and another pair of handles coupled to an outer surface of said bottom wall of said outer housing.

\* \* \* \* \*